United States Patent [19]
Katz

[11] Patent Number: 6,003,525
[45] Date of Patent: Dec. 21, 1999

[54] ELASTOMER FLOSS AND RELATED FLOSSING DEVICES

[76] Inventor: Harry S. Katz, 785 Pleasant Valley Way, W. Orange, N.J. 07052

[21] Appl. No.: 09/039,305

[22] Filed: Mar. 14, 1998

[51] Int. Cl.⁶ ................................................. A61C 15/00
[52] U.S. Cl. ........................... 132/321; 132/323; 132/329
[58] Field of Search ............................ 132/321, 323, 132/324, 325, 328, 326, 327, 329

[56] References Cited

U.S. PATENT DOCUMENTS

| | | | |
|---|---|---|---|
| 788,947 | 5/1905 | Roth | 132/323 |
| 2,811,162 | 10/1957 | Brody | 132/323 |
| 3,800,812 | 4/1974 | Jaffe | 132/321 |
| 3,828,804 | 8/1974 | Ely | 132/323 |
| 3,860,013 | 1/1975 | Czapor | 132/323 |
| 3,930,059 | 12/1975 | Wells | 132/321 |
| 4,013,085 | 3/1977 | Wright | 132/323 |
| 4,142,538 | 3/1979 | Thornton | 132/321 |
| 4,807,752 | 2/1989 | Chodorow | 132/323 |
| 4,817,642 | 4/1989 | Lipp | 132/324 |
| 4,827,952 | 5/1989 | Kos | 132/323 |
| 4,836,226 | 6/1989 | Wolak | 132/321 |
| 4,974,614 | 12/1990 | Selker | 132/321 |
| 5,159,943 | 11/1992 | Richards et al. | 132/321 |
| 5,392,795 | 2/1995 | Gathani | 132/321 |
| 5,545,480 | 8/1996 | Lalani | 132/321 |
| 5,704,379 | 1/1998 | Krynicki | 132/323 |

*Primary Examiner*—John J. Wilson
*Assistant Examiner*—Robyn K. Doan

[57] ABSTRACT

This invention involves a stretchable elastomer floss and elastomer floss disposable units, plus related devices for packaging the floss, dispensing the floss, and for holding the ends of the elastomer floss when the elastomer floss units are in use. The elastomer floss units are manufactured by extrusion or injection molding.

7 Claims, 3 Drawing Sheets

ELASTOMER FLOSS AND RELATED FLOSSING DEVICES

REFERENCES CITED

U.S. PATENT DOCUMENTS
U.S. Pat. No. 3,926,201 December, 1975 Katz . . . 132/323
U.S. Pat. No. 5,246,021 August, 1993 Katz . . . 132/323

BACKGROUND OF THE INVENTION

1. Field of the Invention

This invention relates to elastomer dental floss, disposable flossing units and dental flossing devices. The new elastomer dental floss is effective, and the flossing units are low in cost and disposable.

2. Description of Prior Art

The daily use of dental floss is desirable for a number of reasons. It is a means of cleaning between the teeth and under gum margins so that bacterial or dental plaque is removed. Dental authorities consider plaque the leading cause of periodontal disease and tooth loss in adults. Also, flossing is the best means for removal of food particles after eating. The trapped particles are annoying, may interfere with proper speech, and when permitted to remain, may cause bad breath. The standard wood or plastic tooth picks that have usually been used for this purpose have a number of shortcomings, among them the tendency to break during use, sharp edges that may cut into the gums and cause bleeding, awkward to use and many have a leading point which is often too thick to dislodge particles from narrow spaces between teeth.

The conventional floss for many years, has been a tow or strand of many small diameter nylon filaments. There are minor variations of these floss materials, such as polypropylene filaments instead of nylon filaments, and the addition of a mint or other flavor to the floss, or addition of a coloring pigment or dye. My invention, which is very different from the conventional floss and modifications of current floss, consists of a novel floss material that I designate as "elastomer floss", which can be stretched to squeeze into very narrow spaces between teeth. My invention also includes related devices based on the new elastomer floss innovation.

Prior art in this field discloses that existing disposable dental floss units or floss picks have generally been made by a process that injection molds plastic material around a multiple filament strand of conventional flossing material, producing a chain of floss picks; the floss picks are then separated by cutting apart the floss between a row of floss picks. The following patents represents the state of the art: U.S. Pat. Nos. 3,926,201 and 5,246,021, both granted to Harry S. Katz, the inventor of the present disclosure. Injection molding, as specified in U.S. Pat. No. 3,926,201, is an excellent method for producing this type of product and is one of the preferred methods for manufacturing some of the new products detailed in this invention.

An important point to repeat and emphasize about prior art in this field, is that the use of conventional dental floss, which consists of strands of nylon filaments, has been the overwhelming major means for flossing teeth and between teeth. However, the polymer filaments of conventional dental floss are not sufficiently abrasive to be a highly effective means of removing dental plaque. Especially in view of the fact that most individuals do not have the patience to spend much time on each tooth during flossing. Also, the very small diameter of the conventional floss filaments results in the potential of cutting through the gums of the user, similar to the manner in which a thin wire cutter can be used to cut through cheese, and thus cause bleeding. This is one of many reasons, as further explained below, why this invention provides improvements over the current dental floss and flossing devices.

The present invention is an innovative and non obvious improvement over the prior art of dental flossing materials and devices.

SUMMARY OF THE INVENTION

A primary object of the present invention is to provide a new type of flossing material and products involving my new elastomer floss. It is a further object of this invention to provide low cost and disposable dental flossing units that are readily manufactured in large quantities.

DESCRIPTION OF PREFERRED EMBODIMENTS

FIG. 1 through FIG. 5 are views of typical elastomer floss materials per this invention.

Figure 1:
FIG. 1. is a side angled view of a thin rod or cylindrical extrusion of an elastomer polymer or rubber. The diameter of the continuous length is about 0.06-inch.

These elastomer floss materials are preferably produced by a continuous extrusion process, which is a well known technology in the plastics field. Many different materials can be used. Among these are various flexible plastics, rubbers and elastomers. Preferred materials include FDA approved grades of thermoplastic elastomers such as Kraton G1657 or G2705 produced by Shell Chemical Co., or Vistoflex 671N produced by Advanced Elastomer Systems. FIG. 1 shows a product with a simple circular section, which typically ranges from about 0.010 to 0.090-inch in diameter, with a preferred size of about 0.06-inch diameter or equivalent dimensions in an elliptical, rectangular or other cross section.

Figure 2:
FIG. 2. is a view similar to FIG. 1, wherein there is a filler dispersed in the elastomer, FIG. 3. is a view similar to FIG. 1, where the elastomer has circumferential corrugations that form ridges on the surface.

FIG. 2 shows a similar product, which has a filler in the elastomer floss. A typical filler is pumice, which has been used in the dental industry in tooth polishing compounds. A common procedure by dentists, is to use a small cup of a gel containing pumice and to apply this material to a patient's tooth with a small rapidly-rotating brush. Pumice is a mild abrasive, which does not significantly scratch the tooth surface, but is an effective means for removing dental plaque. A supplier of pumice is C.R. Minerals Corporation, Golden CO. Their Navajo Brand pumice is available in a wide variety of grades, and grades 0, ½, and 1 are suitable choices for this application. Other mild abrasives such as special grades of clay, amorphous silica, and talc can be used. Typical candidate fillers are listed in *THE HANDBOOK OF FILLERS FOR PLASTICS*, Edited by Harry S. Katz and published by Van Nostrand Reinhold, NYC, 1987, and recently distributed by Chapman and Hall, Publishers, London and NYC.

Figure 3:
Figure 4:
FIG. 4. is a view of an extrusion of elastomer or rubber that has a rectangular crosssection.
Figure 5:
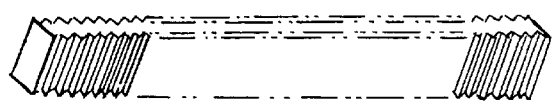
FIG. 5. is a view similar to FIG. 4, wherein there are corrugations that form ridges. on the surface.

FIG. 3 shows a another type of extruded elastomer floss, but with a surface contour that is produced by a post extrusion embossing die. This provides a corrugated surface or can have a threaded rod appearance. FIG. 4 shows a similar product with a rectangular cross section and FIG. 5 shows the product of FIG. 4 that has been embossed on-line by use of a post extrusion process.

Figure 6:
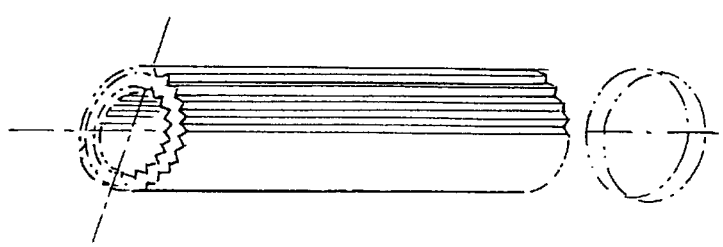
FIG. 6. is a view of a hollow cylindrical extrusion, with longitudinal surface fins or protrusions. The right side of the figure shows one of many thin bands that are sliced or slit from the continuous extrusion.
Figure 7:
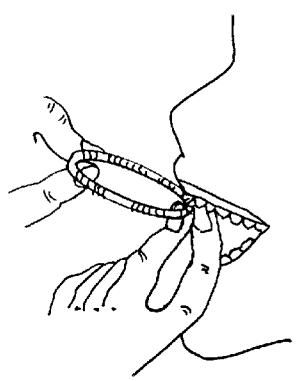
FIG. 7 is a view of a person using the slit band for flossing teeth.

FIG. 6 is a view of an extruded elastomer hollow cylinder with longitudinal fins. This cylinder can be manufactured with various internal diameters and wall thickness. Preferable dimensions are one inch internal diameter, with the cylinder wall thickness of 0.06-inch and triangular fins that protrude to 0.03-inch on both sides of the cylinder wall. This cylinder is cut into narrow bands, preferably 0.06-inch wide, as shown on the right side of FIG. 6. to provide individual flossing units. The use of this type of unit by a person, is illustrated in FIG. 7. These flossing units will be sold with and without a toothpaste or polishing type pumice paste. The paste can be in a separate container or applied to the surface of the floss band surface before final packaging. When sold without a paste coating, the end user may apply a favorite tooth paste or anti-tartar tooth paste to the flossing unit so that the flossing is more effective.

Figure 8:
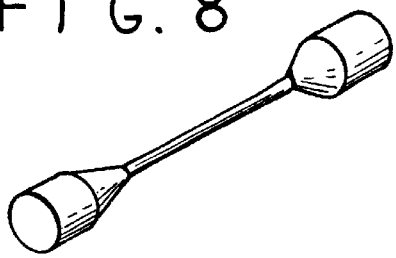
FIG. 8 is a view of an injection molded elastomer flossing unit.
Figure 9:
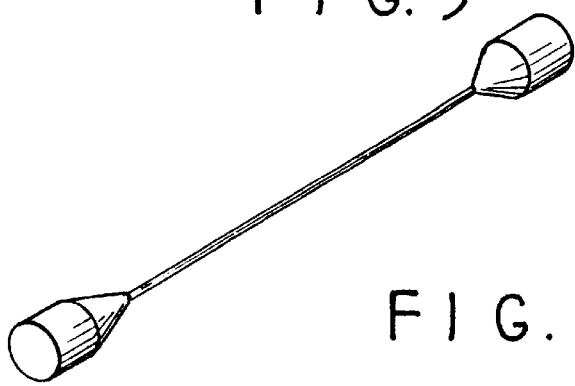
FIG. 9 is a view of the unit shown in FIG. 8 that is stretched in a manner that would be done during use for flossing.
Figure 10:
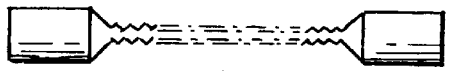
FIG. 10 is a view of a unit similar to FIG. 8, wherein the outer surface of the flossing surface has been molded with circumferential corrugations that provide a rough contoured surface.
Figure 11:
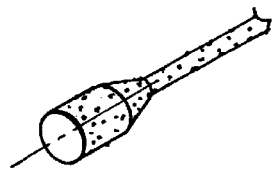
FIG. 11 is a view of a unit similar to the unit shown in FIG. 8, wherein there is a filler dispersed in the elastomer.
Figure 12:
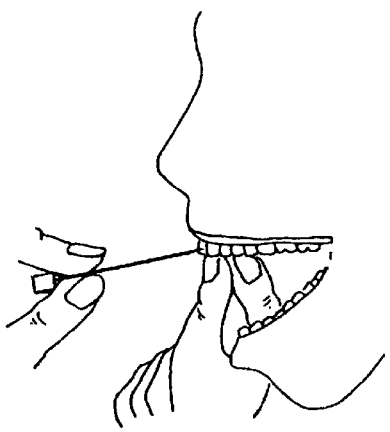
FIG. 12 shows a person using an injection molded flossing unit.

FIG. 8 is a view of an elastomer flossing unit having ends of increased cross section, which is preferably manufactured by an injection molding process. The ends and stretchable length of reduced cross section are formed together of a common material with the ends providing means for holding the flossing unit and for stretching the length. This is preferably manufactured in multi-cavity injection molds in a process that is well known in the plastics industry. The same types of polymers mentioned above are suitable for this molding, although the manufacturers usually recommend a minor variation in the polymer, such as a different molecular weight or melt flow index, for injection molding as compared with an extrusion grade of the same polymer. FIG. 9 is a view of the unit shown in FIG. 8 but in the stretched state that would be involved during the typical use of the unit. FIG. 10 is an injection molded elastomer flossing unit where the flossing surface is modified to have a selected rough surface. In the illustrated FIG. 10, the injection mold cavity to produce this part has been made by drilling a typical hole that is about 0.06-inch in diameter and then using a tap or threading device to provide surface corrugations or roughness. A size 1-64 tap was used to provide surface corrugations for a series of flossing units that were manufactured for some early trials of this invention. The end user can apply a dab of tooth paste to the corrugated length, where the ridges will retain the tooth paste, so that a favorite flavor or odor will be involved during flossing. Also, a brand of tooth paste can be used that will further improve the removal of tartar or plaque. FIG. 11 is an elastomer flossing unit, where the injection moldable elastomer contains a filler to provide a mild abrasive action when the user moves the floss back and forth between adjacent teeth. As noted above, a typical filler is a selected particle size of pumice. FIG. 12 shows an individual using an elastomer flossing unit by holding the ends or tabs of the unit, stretching the unit to provide easy placement between adjacent teeth, and moving the floss back and forth to provide an efficient flossing action.

Figure 13:
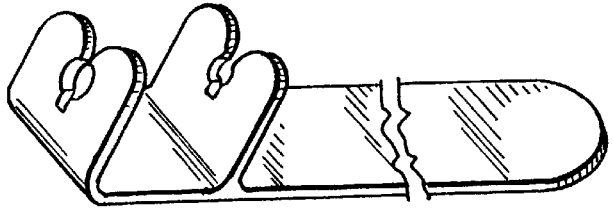
FIG. 13 is a view of an injection molded device that is designed to hold a flossing unit during the flossing procedure.
Figure 14:
FIG. 14. Is a view of a sharp pointed handle that may be molded for the flossing device shown in FIG. 13.

FIG. 13 is a view of a dental flossing device having spaced posts with slots for holding the ends that permits handling convenience for an individual to use elastomer floss injection molded units. The handle end may be round or a pointed end, as shown in FIG. 14, to provide a sharp pick for dislodging food particles.

Figure 15:
FIG. 15. is a view of the flossing device shown in FIG. 13, with an injection molded flossing unit that has been inserted into the device.
Figure 16:
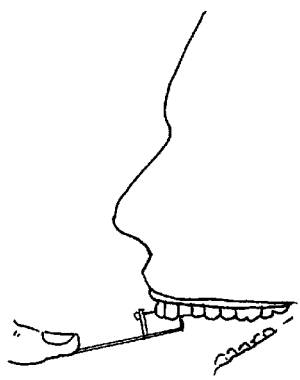
FIG. 16. is a view of a person using the flossing device with the injection molded unit inserted.

FIG. 15 shows an injection molded flossing unit that has been placed into the flossing device by stretching the ends and placing the unit into the retaining slots. FIG. 16 illustrates a user flossing with the elastomer flossing device shown in FIG. 15.

Figure 17:
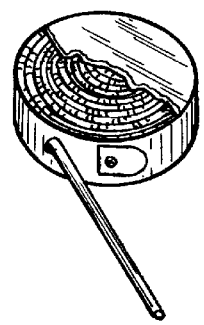
FIG. 17. is a view of a container, including an outer cutting edge, that is suitable for packaging a long length of the extruded elastomer floss.
Figure 18:
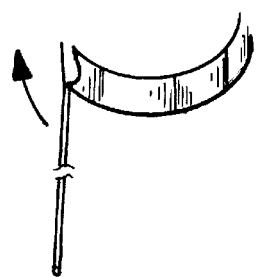
FIG. 18 shows a length of floss from the container of FIG. 17, stretched and cut by the cutting edge.
Figure 19:
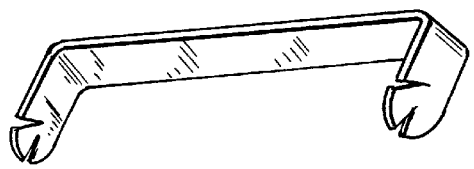
FIG. 19 is a view of a device that is used to hold a length of extruded elastomer floss.
Figure 20:
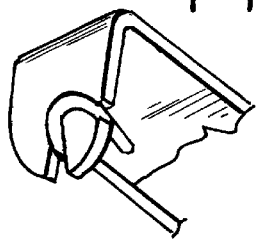
FIG. 20 shows an end of FIG. 19 with slits, wherein the floss can be stretched inserted to hold the floss in place.
Figure 21:
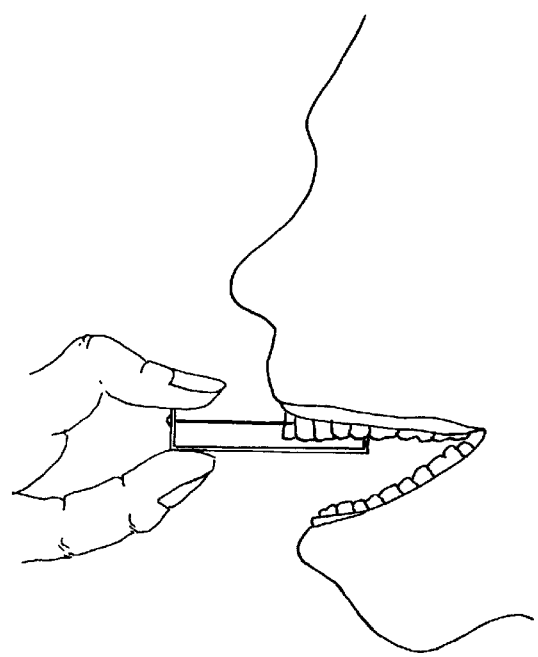
FIG. 21 shows a person using the device shown in FIG. 19 with inserted floss.

FIG. 17 shows a typical container for packaging a rolled length of the elastomer floss extrusion. FIG. 18 shows a cutting device that is located on the outside of the package shown in FIG. 17. FIG. 19 shows a flossing device where the extruded floss can be stretched and the ends pressed into narrow slits in end posts as in FIG. 20, so that the floss is prevented from slipping out of the device while the end user flosses, as shown in FIG. 21.

The preferred elastomers for my elastomer floss invention are olefin thermoplastic elastomer grades that have FDA approval and good elastomeric characteristics. Among the elastomeric characteristics are the ability to be stretched to a moderate elongation or deformed and then return to the original length and shape. Candidate materials were given above. Selected silicone rubber materials are also suitable, but these materials are usually much more expensive than the olefin thermoplastic elastomers that are a preferred material for my invention. Among other suitable materials are polyurethane elastomers and styrene-butadiene thermoplastic elastomers.

The elastomer floss can be used in manners similar to conventional floss. A length of the extruded elastomer floss can be cut and used to floss the teeth. For many end users, it will be preferable to use the injection molded floss units in the floss holding device.

As described above, the preferred manufacturing processes are the extrusion of continuous lengths or cylindrical bands of the elastomer floss and/or injection molding of the elastomer flossing units. The flossing devices are preferably injected molded plastic, but may also be manufactured as machined metal or formed sheet metal devices.

Although this invention has been described with a certain degree of particularity, it is to be understood that the present disclosure has been made only by way of illustration and that numerous changes in the details of the material and method may be resorted to without departing from the spirit and scope of this invention. Also, although this invention is directed primarily to the flossing needs of individuals, These invented products will be suited for many industrial applications where it is desirable to clean narrow spaces within mechanical or electrical equipment.

I claim:

1. A dental floss comprising a filament of elastomeric material having serrated edges throughout a given length and initial cross-section that is stretchable to a reduced cross-section so as to fit between the teeth of a user; the dental floss further including two ends for holding at the length of floss at opposite sides, said ends having a larger cross-section than said initial cross-section of said stretchable filament; said ends being molded in one piece with said stretchable filament, said ends each having a cylindrical portion and a substantially conical portion which tapers from said cylindrical portion down to said initial cross-section of said filament, said cylindrical portions being seized so as to be readily grasped by the fingers of the user.

2. The filament of claim 1 having a cylindrical cross section.

3. The filament of claim 1 having an outer surface with protrusions on said surface.

4. The material of claim 1 having a length stretchable to an elongation of from 20 to 400 percent and having a thickness of from 0.02 to 0.09 inches.

5. The filament of claim 1 having an elliptical cross section.

6. The filament of claim 1 having a rectangular cross section.

7. The filament of claim 1 that contains a mildly abrasive filler within the elastomer.

* * * * *